United States Patent
Blakley (10) Patent No.: US 7,270,005 B2
(45) Date of Patent: Sep. 18, 2007

(54) TRANSDUCER-BASED SENSOR SYSTEM

(75) Inventor: Daniel Robert Blakley, Philomath, OR (US)

(73) Assignee: Hewlett-Packard Development Company, L.P., Houston, TX (US)

(*) Notice: Subject to any disclaimer, the term of this patent is extended or adjusted under 35 U.S.C. 154(b) by 124 days.

(21) Appl. No.: 11/051,787

(22) Filed: Feb. 3, 2005

(65) Prior Publication Data

US 2005/0132812 A1    Jun. 23, 2005

Related U.S. Application Data

(62) Division of application No. 10/355,396, filed on Jan. 31, 2003, now Pat. No. 6,865,949.

(51) Int. Cl.
G01N 29/04 (2006.01)
G01N 29/42 (2006.01)
G01H 13/00 (2006.01)
H03F 3/68 (2006.01)
H04B 1/02 (2006.01)
G01H 11/08 (2006.01)

(52) U.S. Cl. ............... 73/602; 330/295; 455/103; 73/579

(58) Field of Classification Search ............ 73/579
See application file for complete search history.

(56) References Cited

U.S. PATENT DOCUMENTS

| | | | |
|---|---|---|---|
| 3,582,838 A | 6/1971 | DeVries | |
| 3,983,424 A | 9/1976 | Parks | |
| 4,055,072 A | 10/1977 | Fletcher et al. | |
| 4,081,749 A | 3/1978 | Peterson | |
| 4,788,466 A | 11/1988 | Paul et al. | |
| 5,201,215 A | 4/1993 | Granstaff et al. | |
| 5,448,126 A | 9/1995 | Eda et al. | |
| 5,477,098 A | 12/1995 | Eguchi et al. | |
| 5,973,568 A | * 10/1999 | Shapiro et al. | ......... 330/295 |
| 6,144,332 A | 11/2000 | Reindl et al. | |
| 6,636,816 B1 | 10/2003 | Dvorak et al. | |
| 2002/0011761 A1 | 1/2002 | Takeuchi et al. | |

FOREIGN PATENT DOCUMENTS

| | | | |
|---|---|---|---|
| JP | 55-40967 | | 3/1980 |
| WO | WO96/12351 | * | 4/1996 |

(Continued)

OTHER PUBLICATIONS

"In Situ Interfacial Mass Detection With Piezoelectric Transducers", Michael D. Ward et al., Science, vol. 249, Issue 4972, Aug. 31, 1990, pp. 1000-1007.

(Continued)

Primary Examiner—Hezron Williams
Assistant Examiner—Rose M Miller (57) ABSTRACT

A transducer-based sensor system including a drive signal generator for generating a drive signal, a transducer coupled to the drive signal generator and configured to receive the drive signal, a mixer coupled to the transducer and configured to receive output from the transducer where such output results at least in part from physical movement of the transducer, and a diplexer operatively coupled with an output of the mixer and configured to present a substantially matched output impedance to the mixer over an operative range of output frequencies.

17 Claims, 4 Drawing Sheets

FOREIGN PATENT DOCUMENTS

WO    WO 01/02857    1/2001

OTHER PUBLICATIONS

"A Novel Immunosensor for Herpes Viruses", Bernd Konig et al., Analytical Chemistry, vol. 66, No. 3, Feb. 1, 1994, pp. 341-344.

"Piezoelectric Mass-Sensing Devices as Biosensors—An Alternative to Optical Biosensors?", Andreas Janshoff et al., The Quarz-Crystal Microbalance in Life Science, Amer. Chem. Int. Ed. 2000, 39, pp. 4004-4032.

"'Hearing' Bond Breakage, Measurement of Bond Rupture Forces Using a Quartz Crystal Microbalance", F. N. Dultsev et al., Langmuir 2000, 16, pp. 5036-5040.

"Listening for Viral Infection", Erica Ollmann Saphire et al., Nature Biotechnology, Sep. 2001, vol. 19, pp. 823-824.

"Direct and Sensitive Detection of a Human Virus by Rupture Event Scanning", Matthew A. Cooper et al., Nature Biotechnology, Sep. 2001, vol. 19, pp. 833-837.

* cited by examiner

TRANSDUCER-BASED SENSOR SYSTEM

This is a division of application Ser. No. 10/355,396 filed Jan. 31, 2003 now U.S. Pat. No. 6,865,949.

BACKGROUND

Transducer devices are used in a variety of applications to transfer energy between electrical systems and mechanical systems. Quartz crystal microbalance (QCM), for example, is a transducer-based technology that may employ piezoelectric transducers in various configurations to perform sensing functions. QCM technology takes advantage of the fact that the resonant frequency of a transducer typically varies with the effective mass of the transducer. Accordingly, when portions of a sample material bind to the transducer, the mass of the bonded sample material can be detected by monitoring the resonant frequency of the vibrating mass, relative to a predetermined reference.

A related technology is rupture event scanning (RES), in which transducers may be employed to produce mechanical energy to break bonds within a sample material. In addition to providing energy to break the bonds, the transducers may be used as sensors to analyze acoustic events (e.g., a pressure wave) that can occur when bonds break. Different types of bonds have unique properties that produce distinctive acoustic events. The bonds can be identified and analyzed by using various techniques to study the acoustic events.

Transducer systems such as those described above typically employ multiple distinct transducers. The transducers are often provided in an array, with some type of mechanical suspension being used to suspend the transducers in place relative to a base or other stationary component of the system.

Although many prior systems have multiple transducers, typically only one transducer can be activated at any given time. Alternatively, where multiple transducers are simultaneously active, the activated transducers commonly must be separated by a relatively large physical distance. The reason for this is to avoid undesired signal coupling that can occur when physically proximate transducers are active at the same time.

One type of undesired coupling results from the liquid that is often used to hydrate biological samples in QCM and RES applications. Where a well of liquid is spread across multiple transducers, or even where separate liquid wells are employed for each transducer in a multiple-transducer configuration, mechanical vibration produced by one transducer can be transmitted through the liquid (and through intervening structures) to other transducers in the system. Accordingly, when the transducers are simultaneously activated, the electrical signal produced at the second transducer will include interference produced by the vibration of the first transducer. The mechanical suspension that holds the transducers in place can also transmit vibration from one transducer to another, even though such suspensions typically are designed to minimize this effect. Finally, stray capacitance, stray mutual inductance and other indirect electrical coupling can produce interference when physically proximate transducers are activated simultaneously.

Because prior systems typically do not provide for simultaneous activation of physically proximate transducers, they may be limited in processing speed and may not be able to provide a satisfactory level of performance in applications where it is desirable to operate multiple transducers at the same time.

In some prior systems, resolution is limited by the drive signal used to activate the transducers. In particular, the fabrication process and other factors may lead to variations in the resonant frequencies of the transducers in the system. Failure to accommodate these variations can diminish the resolution and/or accuracy of the sensor system. Specifically, when a transducer is activated at frequencies other than its resonant frequencies, the resulting vibration will be less than the maximum possible amount. This can result in lower resolution output signals that are more susceptible to noise.

Other transducer-based sensor systems and methods suffer from disadvantages relating to impedance within the output signal paths for the transducers. In many cases, the impedances within the output signal paths are matched for only a narrow range of output signals. As a result, mismatches and incomplete terminations occur when output signals have characteristics falling outside this range (e.g., frequencies that are higher or lower than the expected range of output frequencies). The signal reflections and other artifacts that can result from the impedance mismatches can significantly complicate the processing of output signals, and can hinder rejection of unwanted noise components.

SUMMARY

A transducer-based sensor system is provided which includes a drive signal generator for generating a drive signal, a transducer coupled to the drive signal generator and configured to receive the drive signal, a mixer coupled to the transducer and configured to receive output from the transducer where such output results at least in part from physical movement of the transducer, and a diplexer operatively coupled with an output of the mixer and configured to present a substantially matched output impedance to the mixer over an operative range of output frequencies.

DETAILED DESCRIPTION

Figure 1:
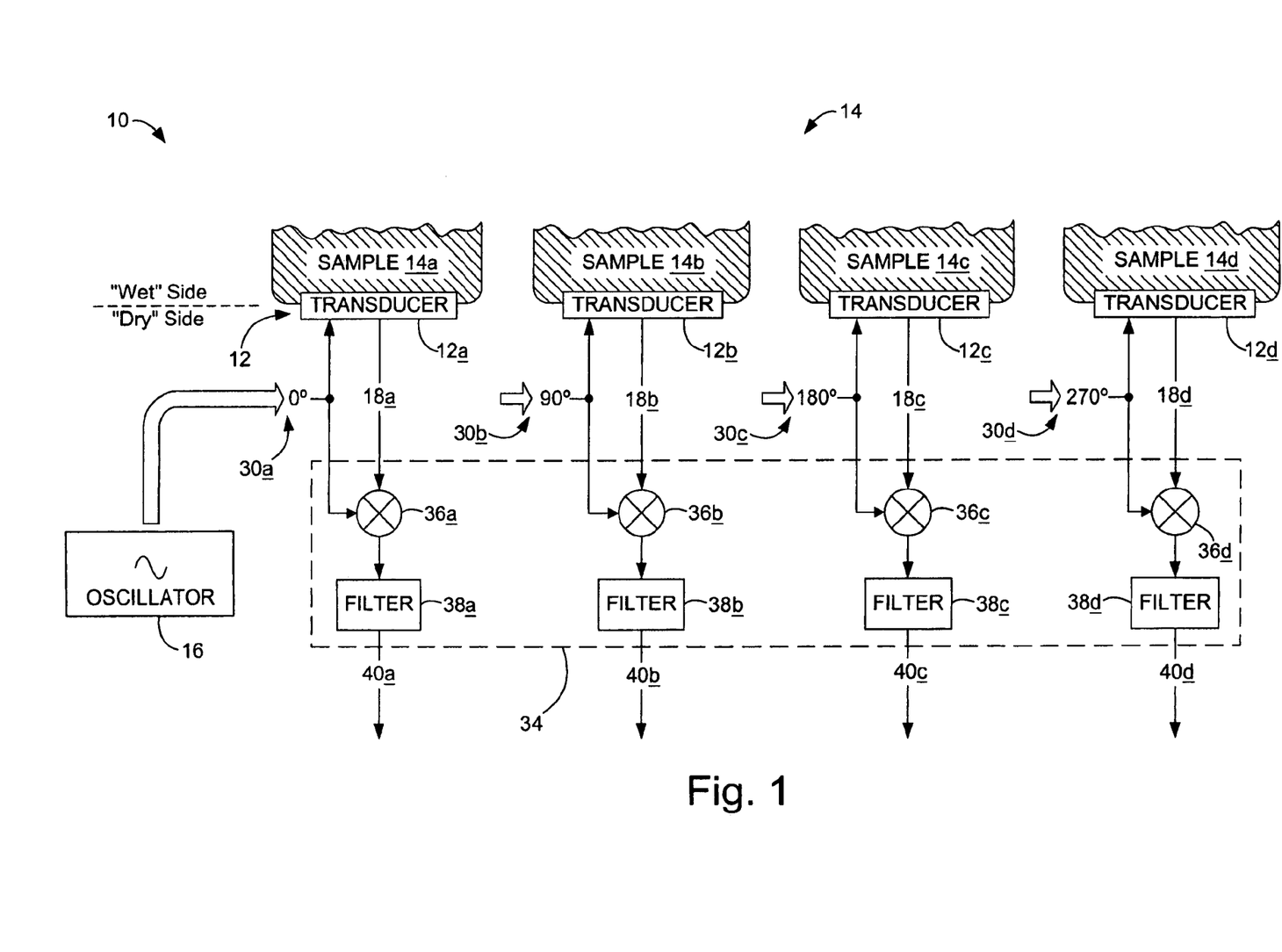
FIG. 1 is a schematic depiction of an embodiment of a transducer-based sensor system.

FIG. 1 depicts an exemplary sensor system 10, including a group 12 of transducers 12a, 12b, 12c and 12d. The transducers may be placed into contact with, or in close proximity to, a test material such as sample 14. The test material may be provided as one contiguous sample spread across multiple transducers, or may be provided as separate portions 14a, 14b, 14c and 14d in a well, receptacle or like container associated with each transducer, as in the depicted example. Typically, the transducers are coupled with a signal generator, such as oscillator subsystem 16, via which activating signals are applied to the transducers. The transducers typically are also coupled with additional electronic components adapted to facilitate sensing functions, as will be explained in detail below.

Figure 2:
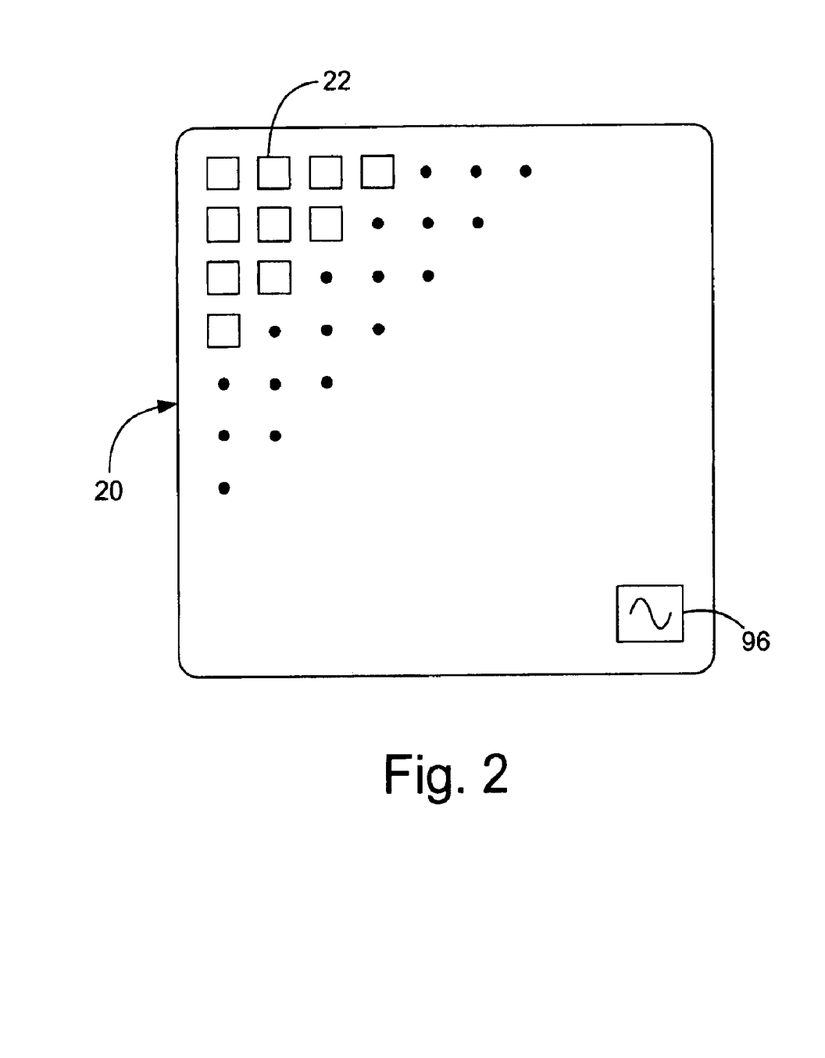
FIG. 2 is a schematic depiction of an embodiment of a transducer array, including a plurality of transducer groups, which may be configured similarly to the transducer group shown in FIG. 1.

The depicted transducers may take a variety of configurations, and may be implemented in different sizes and shapes, and with different materials, as desired and appropriate for a given application. In some embodiments, the transducers are implemented within a microchip as an array of piezoelectric crystals, or as an array of surface acoustic wave devices, surface-skimming bulk wave devices, Love-wave devices or other transducer devices. FIG. 2 depicts such an exemplary array 20, including a plurality of groups 22 of transducers. As with the exemplary group shown in FIG. 1 (i.e., group 12), each of the groups shown in FIG. 2 may include four transducers. Alternatively, any other practicable number of transducers may be employed within the individual groupings. In single-chip embodiments, the supporting electronics typically are implemented at least partially on the chip along with the transducers.

Referring again to FIG. 1, the activating signals applied from oscillator subsystem 16 may cause the transducers to vibrate or undergo other movements. Typically, movement of the transducers is dependent not only on the characteristics of the activating signal, but also on the physical characteristics of the transducer and/or on physical phenomena occurring around the transducer. For example, the response of a transducer to a given activation signal will depend on the resonant frequency of the transducer. Resonant frequency, in turn, varies with the mass bound to the transducer. Accordingly, the character of a transducer's vibration may be affected by matter that bonds to the surface of the transducer to thereby vary the effective mass of the transducer. In addition, phenomena occurring within sample 14, or at the surface of the transducer, can affect transducer movement. For example, breaking of chemical bonds can produce a sonic event (also referred to as an acoustic event) that can contribute to the vibratory movement of a transducer.

In typical embodiments, vibrations and other movement may produce electrical output signals on output lines 18a, 18b, 18c and 18d. Analysis of these electrical signals can produce valuable information about sample 14. For example, such analysis can yield information about whether, and to what extent, portions of the sample have bonded to the surface of the transducers. Information may also be obtained about whether the sample contains certain types of matter, for example, by analyzing signals produced by rupture and other events.

In many applications, to achieve sufficiently accurate sensing, it will be desirable that the signal on any given transducer output line (e.g., lines 18a, 18b, 18c or 18d) correspond only to physical and electrical occurrences associated with the particular transducer, or with phenomena occurring within sample 14 in the immediate vicinity of that transducer. In practice, however, simultaneous operation of more than one transducer can result in cross-transducer noise components on individual transducer output lines. For example, in a non-ideal noisy system, the electrical signal on output line 18a may have components resulting from movement of transducers 12b, 12c or 12d. Because these signal components typically are undesired and correspond to transducers other than transducer 12a, they may be referred to as cross-transducer noise, or cross-transducer noise components.

In many embodiments, the transducers (e.g., transducers 12a, 12b, 12c and 12d) are suspended relative to a base or other stationary structure (not shown) with a mechanical suspension (not shown). Typically, the mechanical suspension is connected to all of the transducers but is designed to allow each transducer to move independently. Moreover, the suspension structure is selected and specifically designed to maximize this independence and thereby minimize crosstalk, or cross-transducer coupling. Although the transducers are substantially independent of one another, there often is some undesired cross-transducer coupling of vibrations and/or other movements through the suspension structure. Vibration of transducer 12a, for example, may couple through the mechanical suspension to produce a vibration in transducer 12b. This would contribute a cross-transducer noise component to the electrical signal on output line 18b.

Typically, the various circuitry coupled with the transducers is at least partially isolated to facilitate obtaining noise-free output signals for each individual transducer. In practice, however, there is often undesired electrical coupling between the circuitry of simultaneously active transducers. This may occur, for example, as a result of stray capacitance, stray mutual inductance, and/or other indirect electrical coupling. Stray capacitance between output lines 18a and 18b, for example, could introduce undesired noise components into the signals on those lines.

In many cases, it will be desirable to employ a liquid within or around sample 14. In biological scanning systems, for example, liquid may be employed to hydrate various types of sample materials. Typically, the liquid is provided within or around each portion of the sample material on one side of the transducer array, such that the transducer array has a "wet side" and a "dry side," as indicated in the example of FIG. 1. Use of such a liquid environment can be another source of cross-transducer noise, as discussed above.

As shown in FIG. 1, oscillator subsystem 16 may be configured to apply different variants of an oscillator signal to the other components of sensor system 10. Typically, the base signal is a sinusoid, and the subsystem generates a number of phase-shifted variants of this signal for use within sensor system 10. As explained in more detail below, the phase-shifted variants may be applied as inputs to produce vibrations or other movement in the transducers. In addition, as also explained below, the phase-shifted variants may be employed during processing of output signals produced by the transducers.

In the depicted embodiment, oscillator subsystem 16 is configured to output four different variants of a sinusoidal local oscillator (LO) signal: (1) a first variant 30a that is in phase with the LO, or 0°, (2) a second variant 30b that is shifted in phase from the LO by 90°, (3) a third variant 30c that is shifted in phase from the LO by 180° and (4) a fourth variant 30d that is shifted in phase from the LO by 270°. These phase-shifted variants typically are all the same frequency as the local oscillator, and may be respectively referred to as the 0° variant, 90° variant, 180° variant and 270° variant.

As shown in FIG. 1, each of the different phase-shifted variants may be applied as an input to a corresponding one of the transducers. In the depicted example, the 0° variant is applied to transducer 12a, the 90° variant is applied to transducer 12b, and so on. As explained below, application of different phase-shifted variants to the transducers may allow an output processing subsystem 34 to isolate and extract output signals from the individual transducers, free from the cross-transducer interference described above.

In order to suppress cross-transducer interference, it will be desirable in many cases to employ the same phase-shifted variants during processing of output signals produced by the transducers. Indeed, exemplary output processing subsystem 34 may be configured to employ the phase-shifted variants to isolate and extract output signals from the transducers.

As in the depicted example, output processing subsystem 34 may include, for each of transducers 12a, 12b, 12c and 12d, a corresponding mixer section (36a, 36b, 36c and 36d, respectively) and a low pass filter (38a, 38b, 38c and 38d, respectively) (LPF). Though depicted as separate devices, the individual mixer devices may be collectively referred to as a mixer, and the individual filter devices may be referred to as a filter. Indeed, the individual devices may be consolidated into one or more single components configured to process multiple signals. The filters may be implemented in a variety of configurations, including configurations incorporating passive and/or active filter components. Filtering may be achieved using a passive RC network, for example. Additionally, or alternatively, active components such as a digital signal processor may be employed to provide filtering. Filtering may be performed based on frequency and/or phase of incoming signals. Indeed, in some embodiments, a digital signal processor is employed to perform linear phase processing, so as to allow for rejection of unwanted signal components. To achieve the desired signal isolation, the digital signal processor may be configured to subtract, for a given transducer output, any out-of-phase, steady-state components. In many cases, frequency filtering using linear-phase topologies or algorithms facilitates channel separation and helps to preserve resultant pulse characteristics. Additionally, in order to achieve adjacent signal rejection in a system employing four simultaneously active channels, it will often be desirable to limit phase deviation of the filter to ±45°.

An exemplary mode of operation for the depicted output processing subsystem will now be described. Referring specifically to transducer 12a, the transducer may be stimulated by application of the 0° variant of the sinusoidal local oscillator signal. This, in turn, results in movement of the transducer. As discussed above, the movement of the transducer may depend on various factors other than the characteristics of the input drive signal. Portions of sample 14 may, for example, bond to the surface of the transducer. The resulting variation in mass (i.e., from an unloaded state) would cause a change in the resonant frequency at which transducer 12a vibrates. In addition, various "acoustic" or "sonic" events can affect the movement of transducer 12a. For example, rupture events at or near the transducer surface (e.g., a portion of sample 14 breaking away from a bonding location on the transducer, or a breaking of chemical bonds within sample 14) may produce a pressure wave that acts upon the transducer.

The various different movements of transducer 12a contribute to the output signal arising on output line 18a. As discussed above, in most cases, it is preferable that the signal on output line 18a reflect only the physical characteristics of transducer 12a and/or events occurring within sample 14 in the immediate vicinity of transducer 12a. However, if transducers other than transducer 12a are simultaneously active, the signal on line 18a will typically include cross-transducer noise (i.e., noise resulting from the other active transducers).

For example, as discussed above, in many implementations, transducers 12a and 12b (as well as transducers 12c and 12d) are operatively coupled to a stationary base with a shared mechanical suspension. Assuming a non-ideal mechanical suspension, vibrations of transducer 12a may cause transducer 12b to vibrate, and/or vice versa, which in turn will contribute noise components to the electrical signals on lines 18a and/or 18b. Noise components can also arise from pressure waves propagating through a liquid sample, and from indirect electrical couplings in the transducer supporting circuitry, as also discussed above.

In many prior systems, these noise issues are avoided by activating only a single transducer at a time, or by ensuring that simultaneously active transducers are spaced apart so that noise contributions are attenuated. This may, however, limit the processing capacity of the sensor system. For example, constraints on the activation of transducers typically will limit the speed of the sensor system. In biological scanning applications, for example, use of such a sensor system may slow scanning operations and produce other processing bottlenecks.

When multiple transducers in the same area are simultaneously active, the depicted use of different phase-shifted variants of the base drive signal facilitates obtaining substantially noise-free output signals. Referring again to transducer 12a and its supporting circuitry, the signal on line 18a is applied to mixer section 36a, along with the same phase-shifted variant 30a (the 0° variant) that was applied as an input drive signal to transducer 12a. Use of the same variant that is used to drive the transducer may be referred to as a "synchronous" deployment within output processing subsystem 34, since the variant typically is in sync with the transducer output signal on line 18a. The mixing at section 36a creates sum frequencies and difference frequencies, which are selectively filtered using LPF 38a. LPF 38a is tuned to pass only a range of frequencies and phase corresponding to transducer 12a. The resulting signal on output line 40a is therefore substantially free of cross-transducer noise.

As indicated above, some cross-transducer noise coupling may occur. However, the predetermined phase differences between the transducer drive signals cause the noise from other transducers to have electrical characteristics that are distinct from the desired base output signal. The characteristics of the noise signal(s) allow the noise to be readily suppressed or removed via the frequency/phase-dependent filtering that occurs at filters 38a, 38b, 38c and 38d. For example, assume transducers 12a and 12b are both activated at the same time with their respective phase-shifted oscillator variants (e.g., variants 30a and 30b). Movements of transducer 12a could produce a noise movement in transducer 12b, via pressure wave coupling occurring through the liquid in sample 14, or through the transducer mechanical suspension. This would contribute noise to the electrical output signal on line 18b. Additionally, or alternatively, a stray capacitance could couple noise onto the output line. However, the phase differences between the oscillator signals used with each transducer would cause such noise contributions to appear on line in a manner that would readily enable the noise to be filtered from the output signal.

More specifically, in certain multiple-transducer embodiments, employing different variants of a periodic signal may cause any "non-pure" (e.g., noisy) transducer output signal to have frequency components that are distinct from those of the noise-free base output. Without noise, for example, the signal on a given output line typically would have a frequency close or identical to that of the base local oscillator signal. Because different transducers within a given group would be driven with different phase-shifted versions of the local oscillator, their vibratory outputs would be staggered in time relative to one another. Accordingly, if vibration from more than one transducer were to contribute to the output on any given transducer output line, the resulting noisy output would have higher frequency components than the noise-free output. The noise components would then be filtered out by the combined operation of the mixer sections and frequency/phase-based filtering.

As indicated above, use of different drive signal variants may be implemented in a number of different ways. The depicted illustrative embodiment may, for example, be extended to more or less than four drive signal variants that are equally distributed in phase over the period of the base oscillator signal. Assuming a modified system with N transducers, the modified system may be implemented with N corresponding drive signal variants, one for each transducer. The drive signal variants would be shifted in phase from the local oscillator by $0°$, $(1/N*360)°$, $(2/N*360)°$, ... and $((N-1)/N*360)°$.

Furthermore, variations other than phase offsets may be employed, such as variations in frequency, amplitude, waveform type, etc. Indeed, the description should be understood to encompass use of any type of drive signal variations that facilitate isolating desired transducer outputs from cross-transducer noise components. Typically, as in the specific illustrative examples above, each transducer within a group is driven by its own unique variant (e.g., a variant that can be distinguished from those used to drive the other transducers within the group). This causes each transducer to have a characteristic response, such that when that response is undesirably coupled into the output channel of another transducer (e.g., as noise), the undesired components on the channel can be readily identified and removed through various techniques, such as frequency/phase-based filtering, adaptive filtering, excitation signal subtraction and the like.

The drive signal circuitry that provides the signal variants to the transducers may also be implemented in many different ways. As shown in FIG. 1, each transducer group 12 may be provided with an oscillator subsystem 16 dedicated to that individual transducer group. Additionally, or alternatively, a global oscillator generator 96 (FIG. 2) may be provided to provide oscillator signals (and variants thereof) to the individual transducer groups 22, via multiplexing, switching and/or other devices/methods.

Figure 3:
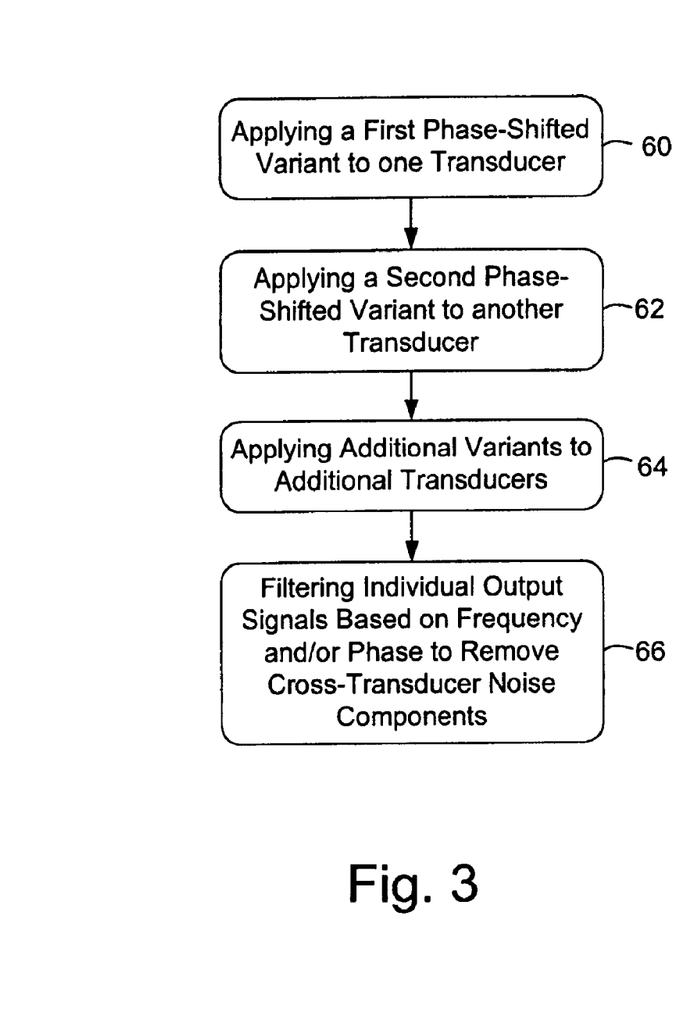
FIG. 3 depicts an exemplary implementation of a multiple-transducer sensing method, in which multiple transducers may be employed at the same time.

A transducer-based sensor method will now be described with reference to FIG. 3. The method may be implemented in a variety of different ways. The following description is merely an illustrative example. As shown at 60 in FIG. 3, the exemplary implementation of the method includes applying a first phase-shifted variant of a periodic signal to a transducer. The implementation also includes applying a second, different variant of the periodic signal to another transducer, as shown at 62. As with the embodiments described above, further variants may be employed as desired and appropriate for a given application, as indicated at 64.

As explained above, the differences between the signal variants typically will cause signals associated with the two transducers to have different characteristics. This, in turn, will cause a noisy output signal (e.g., a signal having components associated with more than one of the transducers) to have characteristics that differ from those of the noise-free signal. Typically, the differences between a noisy signal and a noise-free signal manifest as differences in frequency or frequency ranges, such that noise suppression can be readily performed via bandpass filtering. Indeed, the depicted exemplary implementation includes, at 66, filtering output signals based on frequency to remove cross-transducer noise. Also, as explained above, phase discrimination methods may be employed in addition to or instead of frequency-based filtering.

It should be understood that the depicted implementation can be extended to more than two transducers and two corresponding drive signal variants. For example, as in the exemplary systems described above, it will often be desirable to employ four signal variants (e.g., respectively shifted in phase from a base signal by $0°$, $90°$, $180°$ and $270°$) in a quadrature scheme with groups of four transducers. Indeed, it should be appreciated that the described method may be implemented in connection with the systems described above, and may thus be modified in accordance with the various different configurations that may be employed with those systems. It should be understood, however, that the method is broadly applicable and need not be implemented in connection with the particular systems described above.

It should be understood that the above systems and methods may be applied to a wide variety of multiple-transducer applications where it is desirable to obtain relatively noise-free outputs from individual transducers. As explained in the specific exemplary implementations discussed above, multiple variants of a drive signal are applied to different transducers in the system. Use of the different variations of the drive signal allow signal contributions from the different transducers to have different characteristics. This, in turn, facilitates suppression of noise components, through use of filtering or other techniques.

Figure 4:
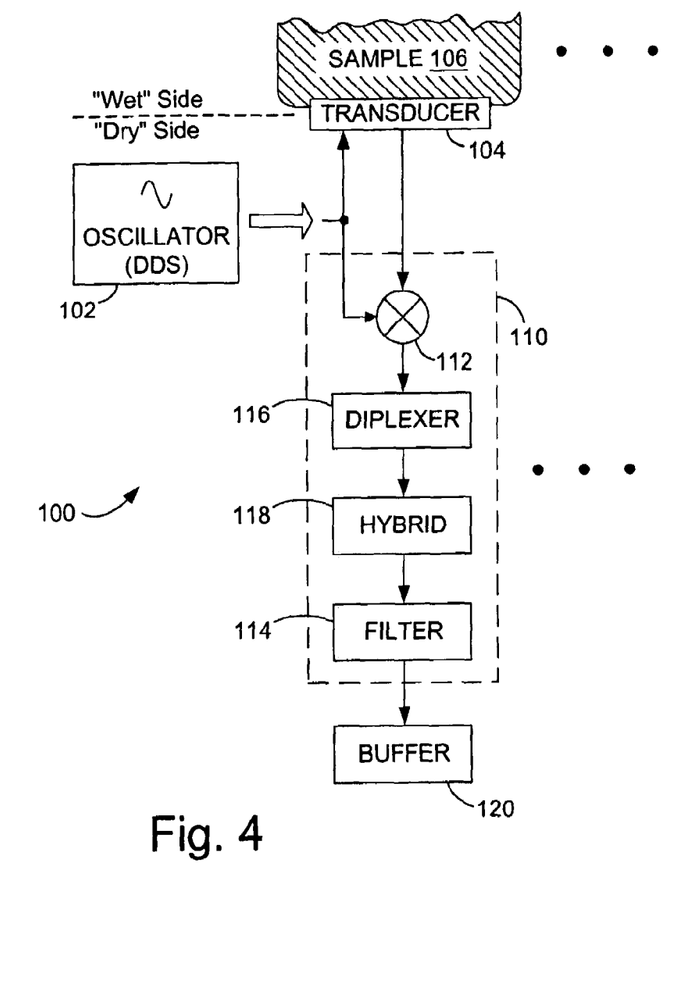
FIG. 4 is a schematic depiction of another embodiment of a transducer-based sensor system.

FIG. 4 depicts yet another embodiment of a transducer-based sensor system 100. Similar to the previously described embodiments, system 100 may include a drive signal generator 102 that is coupled with a transducer 104. Transducer 104 may be placed near or into contact with a sample 106. The drive signal generator produces a drive signal, typically an oscillating sinusoidal signal, which is applied as an input to transducer 104.

Typically, application of the drive signal to the transducer causes the transducer to move. In the case of an oscillatory signal, the resulting movement normally is in the form of reciprocating vibration. Movement of the transducer affects an electrical output signal produced by the transducer. As in the previously described exemplary applications, analysis of the transducer output signal may yield information about the transducer itself, material from sample 106 that has bonded to the transducer, bonds breaking within sample 106, etc.

In many cases, it will be desirable that transducer 104 be driven so as to maximize its mechanical excursions (e.g., so as to cause reciprocal vibrations with as high a physical amplitude as possible). Typically, this will be achieved by driving the transducer with an oscillatory signal tuned to the resonant frequency of the transducer. With many existing silicon fabrication methods, transducer arrays will vary in resonant frequency from batch to batch. Even within a given array, there may be some variation in resonant frequency between transducer groups, or between individual transducers.

Accordingly, drive signal generator 102 may be configured with a programmable capability, in order to ensure that drive signals are provided to yield the desired transducer response. In the depicted example, drive signal generator 102 may be implemented as a direct digital synthesizer (DDS) to facilitate control over the drive signals applied to the transducers. Use of such a device, for example, allows the oscillatory drive signal to be provided at a frequency matched to the resonant frequency of transducer 104, or to some other desired frequency.

The depicted embodiment includes only one transducer, though it will be appreciated that system 100 may be provided with any practicable number of transducers, and transducers may be organized into groups as in the previously described embodiments. Where multiple transducers are employed, the system depicted in FIG. 4 may also be adapted to employ multiple different drive signal variants, as described above with respect to the previous embodiments. Use of a DDS in such a setting can facilitate provision of different drive signal variants (e.g., multiple phase-shifted variants of a base sinusoidal drive signal). For example, use of a DDS readily enables introduction of desired predetermined phase delays to produce drive signal variants.

As in the previously described embodiments, sensor system 100 includes an output processing subsystem 110 configured to process output from transducer 104 (or from multiple transducers). As indicated, output processing subsystem 110 may include a device 112 adapted to receive and process output from transducer 104. In addition, device 112 typically is coupled with signal generator 102, such that the same oscillatory signal that drives the transducer is also applied directly to device 112.

In the depicted example, device 112 is implemented as a mixer. It will be appreciated that the mixed signals in the example are at least substantially synchronous, or contain synchronous components, that is, components of the same frequency and/or phase. Operation of the mixer and accompanying components (to be described) facilitates detection of signals in sync with the base drive signal. Device 112 and its accompanying components may therefore be considered a synchronous detector, or alternatively, a synchrodyne or homodyne.

In the depicted embodiment, mixing of the two signals produces an intermediate output from the mixer that contains components with sum frequencies and difference frequencies. The intermediate output may also vary considerably in the phase relationships of its signal components, relative to the base drive signal. In many implementations, the ability to effectively remove unwanted components from the intermediate output depends on being able to predict how the processing system will perform in the presence of signals with such widely varying characteristics.

In many cases, accurate, noise-free signal extraction will be improved by increasing linearity of various aspects of output processing subsystem 110. This may be accomplished by presenting device 112 with a constant and/or matched output impedance for its expected range of output signals. As indicated above, the provided impedance may be selected to correspond to the varying phase, frequency, and other characteristics of the signal components in the intermediate output generated by device 112. For example, the impedance may be selected to provide linear phase response across desired frequencies, and/or may be selected so as to realize a consistent impedance response across desired frequencies, to thereby maintain signal integrity for the intermediate signal components.

Accordingly, as in the example shown in FIG. 4, output processing subsystem 110 may be provided with an impedance-matching device, such as diplexer 116, which typically is coupled to device 112 (e.g., the mixer) so as to receive the intermediate mixed output. Diplexer 116 may be configured to present a matched and/or constant output impedance to device 112 for the expected operational range of signal components. Without such a matched and/or constant impedance, the termination of the signal channel will be at least partially incomplete, and signal reflections and other effects may occur. These effects can complicate extraction of noiseless output for a given transducer. In sensor applications (e.g., rupture event scanning and quartz crystal microbalance applications), these effects can have an adverse impact on the accuracy of the sensor.

Use of diplexer 116, or a like device, to provide a matched or constant impedance, may be particularly advantageous in a setting where multiple drive signal variants are employed. In the embodiments and method implementations described above, individual transducers within a group may be driven by oscillator variants that are in different phase relationships to the base oscillator drive signal. One potential result of using multiple phase-shifted variants is that the transducer outputs can exhibit a greater variation in characteristics (e.g., phase and frequency) than would be expected if only a single oscillator signal were used to drive the transducers. The increased variation in the characteristics of the intermediate output (e.g., the output from mixer device 112) may complicate design issues relating to the output signal channel. In particular, the increased signal variation increases the potential for a partially non-terminated signal channel, which may lead to the signal reflections and the other undesirable effects discussed above. Provision of the matched and/or constant impedance (e.g., through use of a diplexer for each of the transducers) can stabilize the performance of the output signal channel(s). This stabilization typically will enhance the ability to extract a desired noiseless output, through use of frequency-based filtering, phase discrimination, and the other methods described herein.

Filter 114 may be provided to further facilitate extraction of the desired output signal for transducer 104, or for a given transducer in a multiple-transducer configuration. As in the previously described embodiments, filtering may be performed with a digital signal processor, with active or passive components, and may be performed based on phase and/or frequency to achieve the desired signal isolation.

In some transducer applications, the signal channel may be configured such that both input drive and output response signals coexist on the same channel or signal path. In many cases, this can complicate processing of output signals. For example, in such a setting, it may be difficult to discern whether certain signal characteristics are produced directly by the transducer drive signal, or from movement of the transducer(s). It should be appreciated that the drive signal characteristics normally are known, and therefore are not of interest in most applications. The goal in most sensor applications is not to study the drive signal, but rather to obtain information about the transducer and its immediate environment (e.g., the mass of the transducer, the quantity of sample material that has bonded to the transducer, etc.).

This issue may be addressed with a cyclically repeated "drive and listen" method. In such a method, the transducer(s) is driven via temporary application of the drive signal. Shortly after the drive signal is deactivated, the system response is sampled, for example by reading the output for a given transducer into a storage location, such as FIFO buffer 120. This process is performed repeatedly, to obtain a sample of data over time, and then various time domain and/or frequency domain analyses may be performed on the accumulated data. Depending on the application, the analytical methods that may be applied include Fourier transformations and Hartley/Bracewell transformations, among other methods. In rupture event scanning, for example, these methods may be applied to analyze acoustic emissions produced by rupture or other events.

Figure 6:
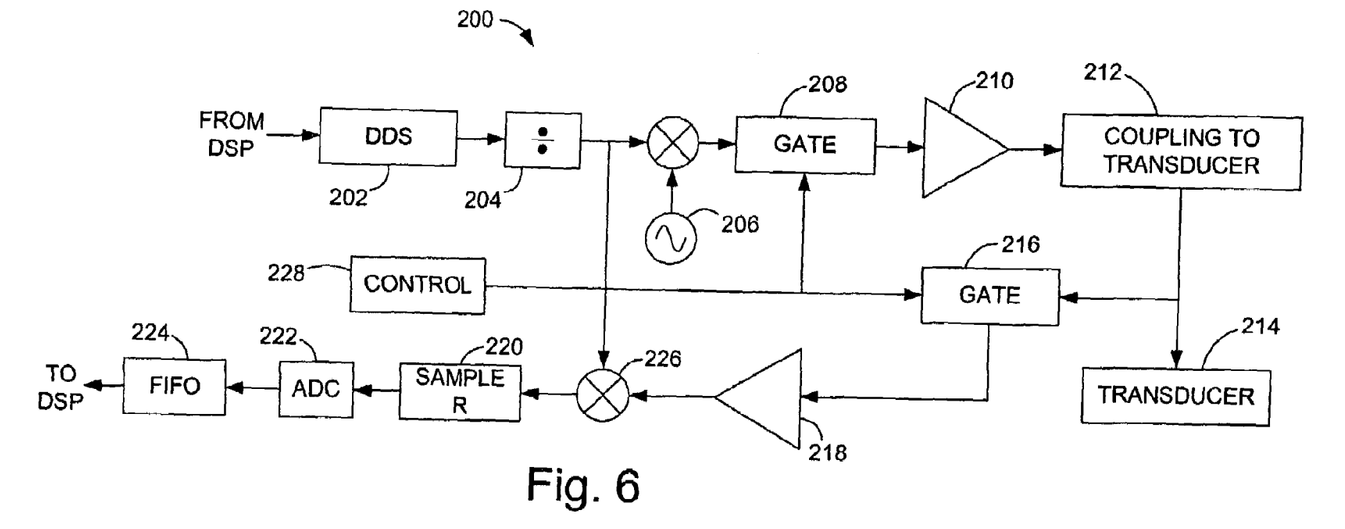
FIG. 6 schematically depicts an exemplary circuit that may be employed to perform sequentially alternating transmission and reception of transducer signals.

FIG. 6 schematically depicts an exemplary circuit 200 that may be used to alternately drive and sample transducer signals. As indicated, circuit 200 typically will include some of the components discussed with reference to the other figures. Referring specifically to the figure, circuit 200 may include a direct digital synthesizer 202 that can be fed with a digital signal processor (DSP) to facilitate generator of transducer drive signals. The generated signal may be processed with a divider 204 and mixed with oscillator 206. The drive signal path may also include a signal gate 208, transducer drive amplifier 210 and coupler 212. Accordingly, drive signals generated by the DSP and oscillator 206 may be applied as inputs to transducer 214. The output signal path may include signal gate 216, amplifier 218, sampler 220, analog-to-digital converter 222 and buffer 224. The resultant sampled output signal can then be applied to the DSP for time domain and/or frequency domain analysis. As indicated, the input signal may be mixed into the output signal path (e.g., via mixer 226), to provide the synchronous detection capability previously discussed. Typically, a controller 228 is also provided to control the timing of the drive and sample cycles.

It will be appreciated that when input drive and output response signals coexist on the same channel or signal path within one of the described systems, that the input and output signals often move in opposite directions. In such a case, it may be advantageous to have a "duplexing" feature, that is, the ability to separate a transmitted or drive signal from the received or resultant signal. Accordingly, a hybrid RF device, such as four-port hybrid RF device 118, may be employed to facilitate segregation of the two signals. The directional nature of the device eliminates the need for the alternating drive and listen method referenced above. Drive signals may be applied to the transducers while simultaneously sampling transducer output. The hybrid RF device may be coupled to the other components in various topologies, though it will often be advantageous to couple the hybrid device to the diplexer output, as in the depicted example.

Figure 7:
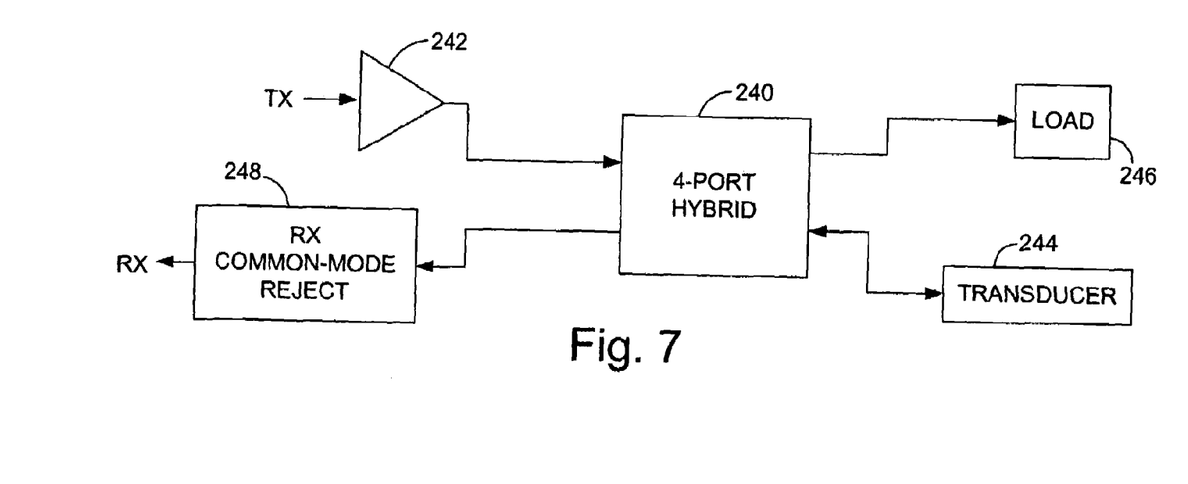
FIG. 7 schematically depicts an exemplary circuit that may be used to sample output from a transducer while simultaneously applying an input drive signal to the transducer.

FIG. 7 depicts an exemplary topology showing how a hybrid RF device may be employed with the systems and methods described herein. As shown, a transducer drive signal (TX) may be applied to 4-port hybrid RF device 240 via transducer drive amplifier 242, in order to drive transducer 244. A resistive load 246 may be coupled to a third port of device 240. The fourth port of device 240 couples into the output signal path. As shown, the output signal path may include a common-mode reject device 248, to facilitate rejection of the input drive signal. Accordingly, the depicted 4-port RF topology allows for simultaneous driving and sampling of transducer 244, while eliminating or at least reducing interference caused by co-existence of input and output signals on the signal channel associated with transducer 244.

It should be further emphasized that the devices and methods described with reference to FIG. 4 may all be advantageously employed in the context of a multiple-transducer system with drive signal variants, such as that described above. Use of matched impedances, for example via diplexer 116, can greatly simplify extraction of noise free transducer outputs in a system employing multiple drive signal variants.

Figure 5:
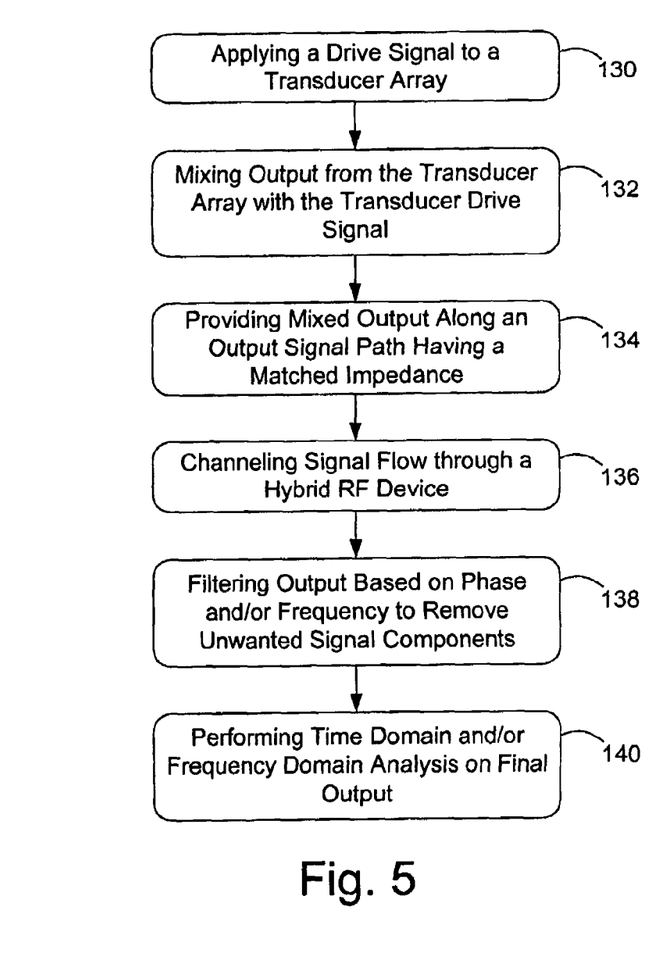
FIG. 5 depicts an exemplary implementation of another transducer-based sensing method.

FIG. 5 depicts another implementation of a sensor method employing one or more transducers. The depicted method may be advantageously employed with the embodiments described above, or in connection with other systems. The method includes, at 130, applying a drive signal to a transducer array. The transducer array may include one or more transducers of any suitable type. As described above, multiple transducers may be employed along with drive signals having varying phase/frequency relationships with a base drive signal.

At 132, the method includes mixing output from the transducer array with the transducer drive signal. This may include, in multiple-transducer embodiments, mixing the output from a given transducer with a copy of the same drive signal variant that was used to drive the transducer. Such an implementation is described with reference to the embodiment of FIG. 1, and particularly in connection with the signals applied as inputs to mixer sections 36*a*, 36*b*, 36*c* and 36*d*.

The mixed output may then be provide along an output signal path having a matched impedance, as shown at 134. In particular, the output signal path may be provided with a diplexer, as discussed above, to provide a matched and/or constant output impedance in the output signal path of the mixing device, for the expected range of signal characteristics. As shown at 136, the method may also include channeling signal flow (e.g., the output from the impedance-calibrated device) through a hybrid RF device. More specifically, in typical implementations of the method, signal flow is provided through a four-port hybrid RF device. The directional characteristics of the hybrid device allow transducer outputs to be sample while simultaneously applying drive signals to the transducers.

As shown at 138 and 140, the method may also include removing unwanted signal components (e.g., to obtain a substantially noise-free output for a given transducer) and performing various types of analysis on the final output. For example, Fourier or Hartley/Bracewell transformations may be applied to the output date to analyze acoustic emissions detected by the transducers. In addition, where frequency-based filtering is employed to remove unwanted signal components, it will often be desirable to employ linear phase filter topologies and/or filtering techniques, as discussed above.

While the present embodiments and method implementations have been particularly shown and described, those skilled in the art will understand that many variations may be made therein without departing from the spirit and scope defined in the following claims. The description should be understood to include all novel and non-obvious combinations of elements described herein, and claims may be presented in this or a later application to any novel and non-obvious combination of these elements. Where the claims recite "a" or "a first" element or the equivalent thereof, such claims should be understood to include incorporation of one or more such elements, neither requiring nor excluding two or more such elements.

What is claimed is:

1. A transducer-based sensor system, comprising:
a transducer configured to produce electrical output based on movement of the transducer;
a synchronous detector operatively coupled to the transducer and configured to produce, in response to application of electrical output from the transducer, plural signal components in an operative range of frequencies, where such plural signal components are subject to subsequent downstream processing to extract a desired, substantially noise-free output signal associated with the transducer; and
a matching device coupled with the synchronous detector and configured to present the synchronous detector with a substantially matched output impedance over the operative range of frequencies, to enhance linearity in processing of electrical output from the transducer.

2. The sensor system of claim 1, where the matching device includes a diplexer.

3. The sensor system of claim 1, further comprising a drive signal generator configured to apply a drive signal to the transducer.

4. The sensor system of claim 3, where the drive signal generator is operatively coupled with the synchronous detector, the synchronous detector being configured to mix the drive signal with electrical output from the transducer.

5. The sensor system of claim 1, further comprising a hybrid RF device positioned within an output signal path associated with the transducer.

6. The sensor system of claim 1, further comprising a plurality of transducer groups, each transducer group including a plurality of transducers, where within each transducer group, each transducer is configured to be drive by a different phase-shifted variant of an oscillatory drive signal.

7. The sensor system of claim 6, where each transducer group includes a first transducer configured to be driven by a variant shifted in phase by 0° from the local oscillator signal, a second transducer configured to be driven by a variant shifted in phase by 90° from the local oscillator signal, a third transducer configured to be driven by a variant shifted in phase by 180° from the local oscillator signal and a fourth transducer configured to be driven by a variant shifted in phase by 270° from the local oscillator signal.

8. The sensor system of claim 6, where each transducer has an associated output signal path, each output signal path including:
  a synchronous detector operatively coupled to the transducer and configured to produce, in response to application of electrical output from the transducer, plural signal components in an operative range of frequencies, where such plural signal components are subject to subsequent downstream processing to extract a desired, substantially noise-free output signal associated with the transducer; and
  a matching device coupled with the synchronous detector and configured to present the synchronous detector with a substantially matched output impedance over the operative range of frequencies, to promote linearity in processing of electrical output from the transducer.

9. A transducer-based sensor system, comprising:
  a plurality of transducers configured to be placed into operative proximity to a sample material;
  a drive signal generator configured to apply electrical drive signals to the transducers to cause the transducers to move; and
  an output processing subsystem configured to process electrical output produced by movement of the transducers, the output processing subsystem including:
    a mixer configured to mix electrical output of at least one of the transducers with an oscillatory signal that is synchronous with an expected component of the transducer's electrical output, the oscillatory signal being thereby configured to facilitate synchronous detection of the expected component, and
    an impedance coupled within an output signal path associated with the at least one of the transducers, the impedance being configured to present a substantially matched output impedance to the mixer over an operative range of frequencies, the impedance being further configured to inhibit signal reflections so as to simplify downstream rejection of unwanted signal components,
  where the drive signal generator is programmable to adjustably provide an oscillatory drive signal having a frequency corresponding to a resonant frequency of one of the transducers.

10. The sensor system of claim 9, where the impedance is implemented with a diplexer coupled within the output signal path.

11. The sensor system of claim 9, further comprising a hybrid RF device coupled within the output signal path.

12. The sensor system of claim 9, where the plurality of transducers are provided in groups, each group containing a plurality of transducers, and where within each group, each transducer is configured to be driven by a different phase-shifted variant of a local oscillator signal.

13. A transducer-based sensor method, comprising;
  producing an electrical output signal based at least in part on movements of a transducer;
  applying the electrical output signal to a synchronous detector;
  applying a local oscillator signal to the synchronous detector, thereby causing the synchronous detector to output plural output signal components in an operative range of frequencies; and
  outputting the plural output signal components to a computing device along an output signal path having an impedance, where the impedance is configured to present a substantially matched output impedance to the synchronous detector over the operative range of frequencies.

14. A transducer-based sensor method, comprising:
  driving a transducer array to cause transducer movement and a corresponding electrical output signal;
  applying the electrical output signal to a synchronous detector;
  applying an oscillatory signal to the synchronous detector, thereby causing the synchronous detector to output plural output signal components in an operative range of frequencies; and
  providing the plural output signal components to a computing device along an output signal path having an impedance, where the impedance is configured to provide a substantially matched output impedance to the synchronous detector for the operative range of frequencies.

15. The sensor method of claim 14, where driving the transducer array includes applying a drive signal to each of a plurality of transducers of the transducer array.

16. The sensor method of claim 15, where driving the transducer array includes applying different phase-shifted variants of a local oscillator signal to transducers within the array.

17. The sensor method of claim 14, where the plural output signal components include unwanted components, the method further comprising performing frequency-based filtering within the output signal path to remove the unwanted components.

* * * * *

UNITED STATES PATENT AND TRADEMARK OFFICE
CERTIFICATE OF CORRECTION

PATENT NO.       : 7,270,005 B2                                           Page 1 of 1
APPLICATION NO.  : 11/051787
DATED            : September 18, 2007
INVENTOR(S)      : Daniel Robert Blakley It is certified that error appears in the above-identified patent and that said Letters Patent is hereby corrected as shown below:

In column 14, line 18, in Claim 13, after "comprising" delete ";" and insert -- : --, therefor.

Signed and Sealed this

Fifth Day of August, 2008

JON W. DUDAS
*Director of the United States Patent and Trademark Office*